(12) United States Patent
Ragab

(10) Patent No.: US 6,346,524 B1
(45) Date of Patent: Feb. 12, 2002

(54) CANCER TREATMENT WITH TEMOZOLOMIDE

(75) Inventor: Mohamed H. Ragab, Westfield, NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 09/535,182

(22) Filed: Mar. 27, 2000

Related U.S. Application Data

(60) Provisional application No. 60/126,808, filed on Mar. 30, 1999.

(51) Int. Cl.$^7$ .............................................. A61K 31/33
(52) U.S. Cl. ...................................................... 514/183
(58) Field of Search ......................................... 514/183

(56) References Cited

FOREIGN PATENT DOCUMENTS

CA         2184545 AA  *  2/1998

OTHER PUBLICATIONS

Dhodapkar et al., Clin. Cancer Res. 3(7), 1093–1100 Abstract Only, 1997.*
Nicholson et al., J. Clin. Oncol., 16(9), 3037–3043 Abstract Only, 1998.*
Newlands et al., Br. J. Cancer 65 (2) 287–291 (1992).
Brock et al., Cancer Research 58, 4363–4367 (1998).

* cited by examiner

Primary Examiner—Jerome D. Goldberg
(74) Attorney, Agent, or Firm—Arthur Mann; William Lee

(57) ABSTRACT

A method for treating a patient afflicted with cancer is provided, in which temozolomide is administered to the patient for at least two cycles of a cyclical dosing schedule, wherein each cycle has a dosing period of 5 to 25 days, in which temozolomide is administered daily, at a dose of 40 to 150 mg/m$^2$/day, followed by a rest period of 5 to 14 days in which temozolomide is not administered.

Also provided is a medical kit for administering temozolomide, having printed instructions for administering temozolomide according to the cyclical dosing schedule set forth above, and a supply of temozolomide in dosage units for at least one cycle, wherein each dosage unit contains 5 to 250 mg of temozolomide and a pharmaceutically acceptable carrier.

11 Claims, No Drawings

CANCER TREATMENT WITH TEMOZOLOMIDE

This application claims the benefit of U.S. Provisional Application No. 60/126,808, filed Mar. 30, 1999.

This invention relates to the treatment of cancer and in particular to the treatment of cancers with Temozolomide.

BACKGROUND OF THE INVENTION

Temozolomide is known for its anti-tumor effects. For example, in one study clinical responses were achieved in 17% of patients having advanced melanoma (Newlands et al. Br. J. Cancer 65 (2) 287–291 (1992)). In another study, a clinical response was achieved in 21% of patients with advanced melanoma (Journal of Clinical Oncology, Vol 13, No. 4 (April), 1995, pp 910–913). Treatment of gliomas in adults with temozolomide is also known (Eur. J. Cancer 1993; 29A:940). Treatment of the following cancers in adults with temozolomide has also been disclosed: metastatic melanoma; high grade glioma, glioblastoma and other brain cancers; lung cancer; breast cancer; testicular cancer; colon and rectal cancers; carcinomas; sarcomas; lymphomas; leukemias; and mycosis fungoides. Prior to the present invention, the generally accepted method for administering temozolomide was to administer it over a 28 day cycle, in which it is administered daily for the first 5 days of the cycle, followed by 23 days of rest, in which it is not administered. Newlands et al., Br. J. Cancer 65 (2) 287–291 (1992). A clinical trial has also been carried out wherein temozolomide was administered continuously as a daily dose for 6–7 weeks in conjunction with radiation treatment. See, e.g., Brock et al., Cancer Research 58, 4363–4367 (1998).

SUMMARY OF THE INVENTION

The present invention provides a method for treating a patient afflicted with cancer, comprising administering temozolomide to said patient for at least two cycles of a cyclical dosing schedule, wherein each cycle comprises a dosing period of 5 to 25 days, in which temozolomide is administered daily, at a dose of 40 to 150 mg/m$^2$/day, followed by a rest period of 5 to 14 days in which temozolomide is not administered.

In a further aspect of the present invention, a medical kit for administering temozolomide is provided, comprising printed instructions for administering temozolomide according to the cyclical dosing schedule set forth above, and a supply of temozolomide in dosage units for at least one cycle, wherein each dosage unit comprises 5 to 250 mg of temozolomide and a pharmaceutically acceptable carrier.

DETAILED DESCRIPTION

The term "temozolomide" is intended to mean a compound having the formula:

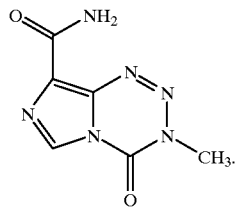

One chemical name for temozolomide is 3,4-dihydro-3-methyl-4-oxoimidazo-[5,1-d] 1,2,3,4-tetrazin-8-carboximide. The synthesis of temozolomide is well known. See, for example, Stevens et al., J. Med. Chem, 1984, 27, 196–201 and Wang et al., J. Chem. Soc., Chem. Commun., 1994, pp 1687–1688.

As used herein, the term "mg/m$^2$/day" refers to a daily dose measured in milligrams per square meter of body surface area of the patient.

As used herein, the term "patient" refers to a mammal, preferably a human.

Examples of cancers treatable by this invention include, but are not limited to melanoma; high grade glioma, glioblastoma and other brain cancers; lung cancer; breast cancer; testicular cancer; gastro intestinal cancers including colon, rectal, pancreatic, and gastric cancers, hepatocellular carcinoma; head and neck cancers; prostate cancer, renal cell carcinoma; adenocarcinoma; sarcomas; lymphomas; leukemias; and mycosis fungoides. This invention contemplates treating these cancers and other cancers at any stage from the discovery of the cancer to the advanced stage. The invention includes treatment of the primary cancer and metastases thereof.

A person afflicted with cancer may exhibit one or more of the following signs or symptoms:

(a) presence of cancerous tumor,
(b) fatigue,
(c) pain,
(d) decreased performance status from tumor burden, and
(e) the well known symptoms associated with each specific cancer.

The rest period according to the present invention (the portion of the cycle in which temozolomide is not administered) is 5 to 14 days, more preferably, 5 to 10 days, most preferably, 1 week. The dosing period according to the present invention is 5 to 25 days, more preferably, 1, 2, or 3 weeks, most preferably 1 or 3 weeks. The treatment cycles may be continued for as long as needed to cause the cure, remission, or elimination of the cancer that is being treated.

The daily dose during the dosing period of the present invention is 40 to 150 mg/m$^2$/day, more preferably 40 to 125 mg/m$^2$/day, most preferably 75 to 125 mg/m$^2$/day. The daily dose may be administered as a single dose, or as multiple doses adding up to the single dose. For example, a daily dose of 100 mg/m$^2$ may be administered as two doses of 50 mg/m$^2$, or four doses of 25 mg/m$^2$. The selected dosage may be decreased, if intolerable side effects or hematologic toxicity are encountered.

A common, but tolerable side effect of temozolomide is nausea and vomiting. This can be alleviated by administering an anti-emetic in conjunction with the temozolomide. It is preferred that the anti-emetic Ondansetron be given p.o. in a dose of about 8 mg about 30 minutes before temozolomide administration. Other anti-emetics such as Hasaldol, Benadryl, and Ativan may also be used as needed.

Temozolomide is preferably administered orally in capsule form wherein it is admixed with conventional pharmaceutical carriers. Preferred temozolomide capsule formulations are:

| Ingredient | mg/Capsule | | | |
|---|---|---|---|---|
| temozolomide | 5 | 20 | 100 | 250 |
| Anhydrous Lactose NF | 132.8 | 182.2 | 175.7 | 154.3 |
| Sodium Starch Glycolate NF | 7.5 | 11.0 | 15.0 | 22.5 |
| Colloidal Silicon Diozide NF | 0.2 | 0.2 | 0.3 | 0.7 |

-continued

| Ingredient | mg/Capsule | | | |
|---|---|---|---|---|
| Tartaric Acid NF | 1.5 | 2.2 | 3.0 | 9.0 |
| Steric Acid NF | 3.0 | 4.4 | 6.0 | 13.5 |
| Capsule Size* | 3 | 2 | 1 | 0 |

*White opaque, preservative-free, two-piece hard gelatin capsules

Other forms of administration of temozolomide, as they become available, are contemplated, such as by IV injection or infusion, intrathecally, by sustained release dosage form, syrup, suppository, transdermal, nasal spray, etc.. Any form of administration will work so long as the proper dosage is delivered without destroying the temozolomide.

It may be preferable in some instances to administer an initial large oral bolus dose of about 100 to 500 mg/m$^2$ prior to beginning the cyclical dosing regimen of the present invention.

The medical kit in accordance with the present invention may be in any form suitable for providing a supply of temozolomide for at least one cycle, together with written instructions for administering it according to the cyclical dosing schedule. Examples include, but are not limited to, various containers (e.g., bottles, cartons, blister packs, and ampules) either accompanied by a package insert describing the cyclical dosing instructions, or wherein the cyclical dosing instructions are printed on, or affixed to the container.

The following examples illustrate the foregoing invention, although such examples should not be construed as limiting the scope of the invention.

EXAMPLE 1

To a patient suffering from glioma, administer temozolomide for a period of twelve 14-day cycles, each cycle consisting of a one week period in which temozolomide is administered at the rate of 100 mg/m$^2$/day, followed by a one week rest period in which temozolomide is not administered.

EXAMPLE 2

To a patient suffering from glioma, administer temozolomide for a period of six 28-day cycles, each cycle consisting of a three week period in which temozolomide is administered at the rate of 100 mg/m$^2$/day, followed by a one week rest period in which temozolomide is not administered.

EXAMPLE 3

To a patient suffering from advanced melanoma, administer temozolomide for a period of twelve 14-day cycles, each cycle consisting of a one week period in which temozolomide is administered at the rate of 100 mg/m$^2$/day, followed by a one week rest period in which temozolomide is not administered.

EXAMPLE 4

To a patient suffering from advanced melanoma, administer temozolomide for a period of six 28-day cycles, each cycle consisting of a three week period in which temozolomide is administered at the rate of 100 mg/m$^2$/day, followed by a one week rest period in which temozolomide is not administered.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:

1. A method for treating a patient afflicted with cancer, comprising administering temozolomide to said patient for at least two cycles of a cyclical dosing schedule, wherein each cycle comprises a dosing period of 5 to 25 days, in which temozolomide is administered daily, at a dose of 40 to 150 mg/m$^2$/day, followed by a rest period of 5 to 14 days in which temozolomide is not administered.

2. The method of claim 1, wherein the rest period is 5 to 10 days.

3. The method of claim 2, wherein the daily dose is 75 to 125 mg/m$^2$/day.

4. The method of claim 1, wherein the rest period is one week.

5. The method of claim 4, wherein the daily dose is 75 to 125 mg/m$^2$/day.

6. The method of claim 1, wherein the dosing period is one, two, or three weeks.

7. The method of claim 6, wherein the rest period is one week.

8. The method of claim 7, wherein the dosing period is one week.

9. The method of claim 8, wherein the daily dose is 75 to 125 mg/m$^2$/day.

10. The method of claim 7, wherein the dosing period is three weeks.

11. The method of claim 10, wherein the daily dose is 75 to 125 mg/m$^2$/day.

* * * * *

(12) EX PARTE REEXAMINATION CERTIFICATE (5190th)
United States Patent
Ragab

(10) Number: US 6,346,524 C1
(45) Certificate Issued: Aug. 23, 2005

(54) CANCER TREATMENT WITH TEMOZOLOMIDE

(75) Inventor: Mohamed H. Ragab, Westfield, NJ (US)

(73) Assignee: Schering Corporation, Kenilworth, NJ (US)

Reexamination Request:
No. 90/006,938, Feb. 17, 2004

Reexamination Certificate for:
Patent No.: 6,346,524
Issued: Feb. 12, 2002
Appl. No.: 09/535,182
Filed: Mar. 27, 2000

Related U.S. Application Data

(60) Provisional application No. 60/126,808, filed on Mar. 30, 1999.

(51) Int. Cl.$^7$ .............................................. A61K 31/33
(52) U.S. Cl. ..................................................... 514/183

(56) References Cited

FOREIGN PATENT DOCUMENTS

| CA | 2184546 | * | 2/1998 |
|----|---------|---|--------|
| WO | WO 97/12630 | | 10/1997 |

OTHER PUBLICATIONS

Wedge et al. Cancer Chemotherapy and Pharmacology vol. 40, No. 3, (1997), pp. 266–272.
Newlands et al., Cancer Treatment Reviews vol. 23, No. 1, (1997) 35–61.

International Search Report for PCT/US 00/08079 (OC01017Q), international filing date Mar. 27, 2000, 8 Pages.

Written Opinion for PCT/US 00/08079 (OC01017Q), international filing date Mar. 27, 2000, 6 pages.

International Preliminary Examination Report for PCT/US 00/08079 (OC01017Q), international filing date Mar. 27, 2000, 7 pages.

XP–002156887 Abstract of CA19962184546.

* cited by examiner

*Primary Examiner*—Dwayne Jones

(57) ABSTRACT

A method for treating a patient afflicted with cancer is provided, in which temozolomide is administered to the patient for at least two cycles of a cyclical dosing schedule, wherein each cycle has a dosing period of 5 to 25 days, in which temozolomide is administered daily, at a dose of 40 to 150 mg/m$^2$/day, followed by a rest period of 5 to 14 days in which temozolomide is not administered.

Also provided is a medical kit for administering temozolomide, having printed instructions for administering temozolomide according to the cyclical dosing schedule set forth above, and a supply of temozolomide in dosage units for at least one cycle, wherein each dosage unit contains 5 to 250 mg of temozolomide and a pharmaceutically acceptable carrier.

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–11 is confirmed.

\* \* \* \* \*